United States Patent [19]

McFarlane

[11] Patent Number: 4,767,408
[45] Date of Patent: Aug. 30, 1988

[54] FLASHBACK STRUCTURE

[75] Inventor: Richard H. McFarlane, Geneva, Ill.

[73] Assignee: Taut, Inc., Geneva, Ill.

[21] Appl. No.: 128,004

[22] Filed: Nov. 27, 1987

Related U.S. Application Data

[63] Continuation-in-part of Ser. No. 843,493, Mar. 24, 1986, Pat. No. 4,710,173.

[51] Int. Cl.$^4$ ............................................. A61M 5/00
[52] U.S. Cl. ........................................ 604/168; 604/900
[58] Field of Search ............... 604/168, 52, 53, 900, 604/169

[56] References Cited

U.S. PATENT DOCUMENTS

| | | | |
|---|---|---|---|
| 4,269,186 | 5/1981 | Loveless et al. | 604/168 |
| 4,365,630 | 12/1982 | MacFarlane | 604/168 |
| 4,525,157 | 6/1985 | Vaillancourt | 604/168 |

Primary Examiner—Stephen C. Pellegrino
Attorney, Agent, or Firm—John Cyril Malloy

[57] ABSTRACT

A flashback structure of the type primarily designed to be used in combination with a catheter assembly and more specifically structured to provide clear visual indication of blood flow along a circuitous path of fluid flow which is indicative of proper placement of the sharpened tip of a needle in a blood vessel. Blood flow is retained within the path of fluid flow by a cover sleeve disposed in covering relation to the flow path.

8 Claims, 2 Drawing Sheets

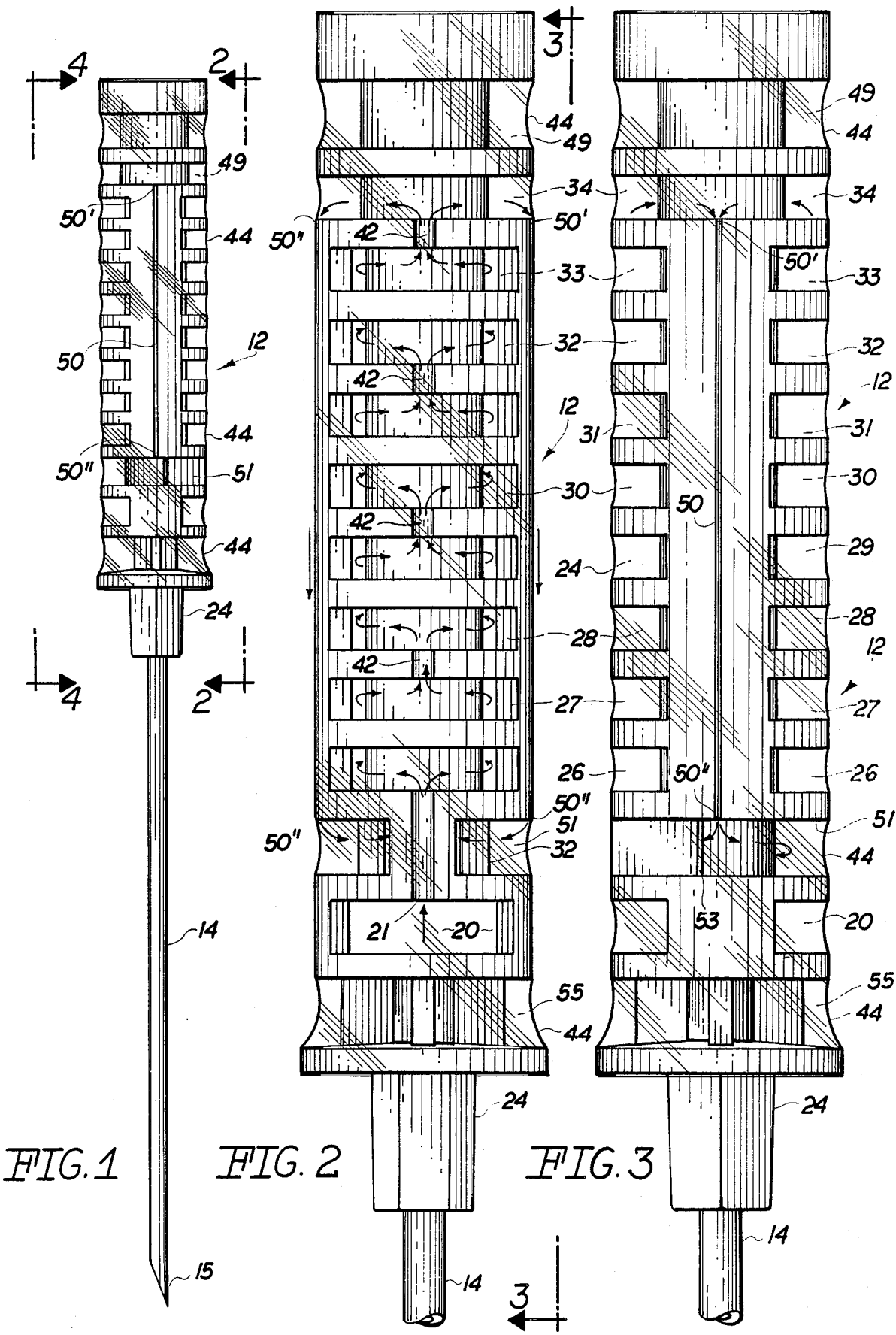

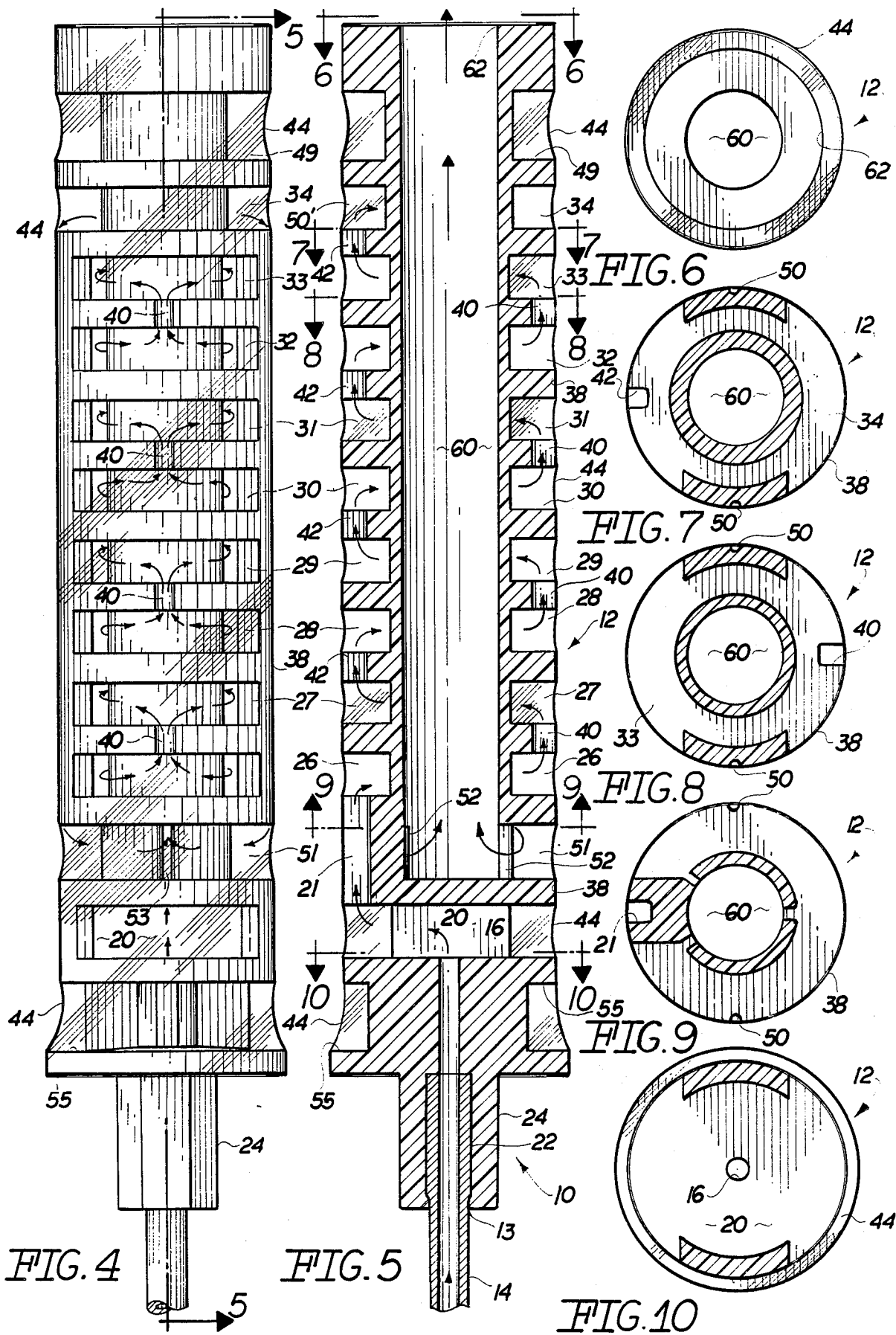

FLASHBACK STRUCTURE

BACKGROUND OF THE INVENTION

This is a continution in part application of presently pending patent application Ser. No. 843,493 filed on Mar. 24, 1986 now U.S. Pat. No. 4,710,173.

FIELD OF THE INVENTION

This invention relates to a flashback structure of the type formed specifically on the base member attached to a proximal end of a hollow needle having a sharpened tip at the distal end thereof and further wherein the base and needle structure are primarily designed for the support and placement of a catheter assembly properly within a blood vessel. A fluid flow channel is formed in a circuitous configuration on the base and disposed and structured for visual observation of blood entry and travel along the flow channel wherein such proper flow is indicative of proper placement of the sharpened tip within the blood vessel.

DESCRIPTION OF THE PRIOR ART

In the utilization of a catheter assembly to the extent of proper placement of the catheter assembly, the sharpened tip of the supporting needle or cannula on which the catheter structure is mounted first penetrates the designated blood vessel. When the sharpened tip is properly positioned, blood flows continuously through the hollow support needle from the tip to a proximal end thereof which is fixedly attached to a gripping base. The blood passing from the blood vessel through the needle will continue to flow into any receiving chamber or cavity. Such flow characteristics allows the medical personnel applying the catheter to visually observe the blood flow. If the flow is continuous, the user knows that the tip of the needle is properly positioned in a vein or artery and the catheter, coaxially disposed about the penetrating needle is ready for subsequent advancement into the vein or artery in which the needle tip has been properly positioned.

Visual observation of incoming blood flow is recognized as an efficient and proper means of determining whether the sharpened tip of a needle is positioned within the blood vessel of the patient. There is a need in the medical profession for what may be termed a flashback structure which is specifically designed to enhance or facilitate the visual observation of blood flow from the needle into the base or gripping portion of the catheter assembly. Such a flashback structure ideally should be capable of providing observation, not only of the initial start of blood flow, but the determination that the incoming blood is in a state of continuous flow as the blood passes from the proximal end of the catheter into the flashback structure. For example, in such instances where the sharpened tip passes completely through the blood vessel, there will be an initial flow of blood passing through the needle and into the leading end of the flashback structure or chamber. However, if the path of fluid flow of the blood entering the flashback chamber or cavity is not properly designed, visual observation to determine whether the blood flow is initial or continual may be difficult.

In the prior art, U.S. Pat. No. 4,365,630 to McFarlane discloses a flashback chamber providing a substantially circuitous path of blood flow as it enters the base of the flashback chamber. While efficient and operable for its intended function, the structure disclosed in the above noted patent may also be somewhat difficult and/or expensive to produce due to the relatively complex structure in forming the preferred circuitous path of blood flow used to enhance visual observation thereof.

Accordingly, there is still a need in the medical profession for a flashback structure of a simplified design and construction yet which may facilitate visual observation of blood flow to the extent that determination of continuous blood flow is readily accomplished.

SUMMARY OF THE INVENTION

The flashback structure of the present invention is, as generally set forth above, designed for use primarily in combination with a catheter assembly. The referred to catheter assembly is not specifically shown, for purposes of clarity, but is of the type including a catheter hub disposed in coaxial, jacketed and slidable relation about a hollow needle. The referred to needle has a distal end or tip which is sharpened to facilitate penetration and entry of the needle into the blood vessel of the patient. The proximal end of the needle is mounted on the interior of a base portion and, due to the fact that the needle is hollow along its entire length, blood flow, after entry of the sharpened tip into the blood vessel, occurs along the full length of the needle into the interior of the base as it flows from the proximal end secured to the base.

A flow channel is formed on the base and is structured to define a path of fluid flow of the blood passing from the proximal end of the hollow needle. More specifically, the path of fluid flow is specifically designed to have a circuitous configuration thereby facilitating visual observance of the movement or passage of the blood along the length of the flow channel as well as coagulation thereof to reduce the possibility of blood leakage from the base.

An important feature of the present invention is the provision of the flow channel being defined by a groove structure formed in the outer surface of the base and being dimensioned to extend into the base a sufficient depth to facilitate free flow of the blood along substantially the entire length of the base as it leaves the proximal end of the needle. The aforementioned circuitous path is defined by the groove structure and preferably comprises a plurality of groove segments disposed in substantially transverse relation to the length of the base and in at least partially surrounding relation thereto as each of the groove segments is disposed in spaced apart relation to one another in the cylindrically configured exterior surface of the base.

A vent means is formed in direct fluid communication with the flow channel so that air being forced from the flow channel as blood enters therein can readily pass from the base to the exterior thereof. Again, in a preferred embodiment of the present invention to be described in greater detail hereinafter, the vent means comprises a vent groove also formed in the exterior surface of the base but being of a significantly lesser depth than any of the groove segments. The dimension or depth of the groove in the external surface of the base is sufficient to allow free passage or flow of air therealong to a vent port which communicates with the exterior of the base through a hollow interior portion thereof. However, the depth or dimension of the vent groove is such as to allow but substantailly restrict blood or liquid flow therealong in order to hamper or delay the time required for the blood to reach the aforementioned vent port. Obviously, it would be a disadvantage if blood were to flow freely from the base or "leak" therefrom. Accordingly, the flow of blood is restricted, as it travels along the length of the vent groove, serving to lengthen the time of travel thereby encouraging hardening or coagulation of the blood and minimizing the amount of blood, if any, which actually exits the base. Another structural feature of the present invention is the provision of a cover means in the form of an elongated sleeve disposed in covering relation to substantially the entire outer cylindrical surface of the barrel-like base and in overlying and covering relation to the vent groove as well as the flow channel to restrict fluid flow therealong. The covering sleeve may in fact be heat sealed in its overlying and covering relation as will be explained in greater detail hereinafter. Preferably, eat shrinkable tubing is utilized.

After experimentation with the structure of the present invention, it has also been found that the circuitous path of travel, which may in part be due and defined by the curvilinear or semiannular groove segments serve to additionally aid in the coagulation of the blood as it passes along the flow path prior to it having a chance to enter into the central interior channel of the base. This also aids in the prevention of any blood actually leaking from the base which is of course undesirable especially in light of the recent avoidance of all hazardous conditions which may contribute to the spreading of ACQUIRED IMMUNE DEFICIENCY SYNDROME (AIDS).

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a front plan view of the flashback structure of the present invention.

FIG. 2 is a front plan view of the base of the embodiment of FIG. 1 in partial cutaway and along line 2—2 of FIG. 1.

FIG. 3 is a front plan view in detail and partial cutaway of the base portion of the present invention.

FIG. 4 is a longitudinal side view along line 4—4 of FIG. 1.

FIG. 5 is a longitudinal sectional view along line 5—5 of FIG. 4.

FIG. 6 is an end view along line 6—6 of FIG. 5.

FIG. 7 is a sectional view along line 7—7 of FIG. 5.

FIG. 8 is a sectional view along line 8—8 of FIG. 5.

FIG. 9 is a sectional view along line 9—9 of FIG. 5.

FIG. 10 is a sectional view along line 10—10 of FIG. 5.

Like reference numerals refer to like parts throughout the several views of the drawings.

DETAILED DESCRIPTION OF THE PREFERRED EMBODIMENT

As shown in FIGS. 1, 2 and 3, the flashback structure of the present invention is generally indicated as 10 and includes a base 12 which is preferably formed from a rigid material and which is fixedly secured to an elongated hollow needle 14 having a proximal end secured within base 12 as at 13. The proximal end 13 is disposed in fluid communication with a receiving channel 16 for the directing of fluid flow, such as inflowing blood, into the base 12 and more specifically, into the beginning of a flow channel through a connecting port 20.

The opposite or distal end of needle 14 has a sharpened tip 15 to facilitate penetration and entry of the tip into a designated blood vessel of the patient. Once so positioned and as pointed out above, proper entry and positioning of the tip 15 into the blood vessel establishes a continuous flow of blood through the sharpened tip 15, along the length of the needle 14, and out of the proximal end 13 into the receiving channel 16. Proper securement of proximal end 13 of needle 14 in the position shown in FIG. 3 is accomplished by an adhesive, friction, or like fit or attachment as at 22 between outstanding nose portion 24 at the leading end of the base 12 and the exterior surface of the needle 14.

An important feature of the present invention is the provision and structure of the flow channel. The flow channel is clearly indicated by the directional arrows of FIGS. 2, 4 and 5 and comprises a groove structure which preferably includes a plurality of groove segments 26 through 34 (actual number may vary), each having a curvilinear or semi-circular, arcuate configuration. Each of the groove segments are integrally formed in the exterior, cylindrical surface 38 of the base 12, the configuration of which may be termed a substantially barrel type configuration.

It should be noticed that though the plurality of groove segments 26 through 34 collectively extend along the length of the base 12, each groove extends in at least partially surrounding relation to the longitudinal axis of the base 12 due to its curvilinear or semi-circular configuration.

Further with reference to FIGS. 2, 4 and 5, a circuitous path of travel of incoming blood is defined as it flows along the length of the flow channel in that adjacently positioned pairs of groove segments are interconnected in fluid communication with one another by a plurality of connecting ports 40 interconnecting adjacent pairs of grooves 26, 27; 28, 29; 30, 31; and 32, 33 at one end of the adjacent pairs as set forth above. In addition, a plurality of connecting ports 42 are located at the opposite end of additional adjacent groove segments 27, 28; 29, 30; 31, 32; and 33, 34 (see FIGS. 2 and 5). Therefore, it is readily apparent, primarily from the directional arrows in FIGS. 2, 4 and 5, that the direction of travel of the blood as it passes along the length of the flow path is successively reversed as it passes through the successive connecting ports 40 and 42 at opposite ends of the grooves 26 through 34. A circuitous path of fluid flow is thereby established as the blood travels along the length of flow channel 25. In order to retain fluid flow throughout the flow channel 25 generally and particularly through the plurality of groove segments 26 through 34, a cover means is provided in the form of an elongated sleeve 44 open at both ends and positioned in surrounding relation to the exterior, cylindrical surface of the base 12. In a preferred embodiment, the sleeve 44 is formed from an at least partially transparent material capable of being heat shrunk and thereby permanently affixed to the exterior cylindrical surface 38 in covering relation to each of the groove segments 26 through 34. As clearly shown, the covering disposition of the sleeve 44 relative to the open side of the groove segments serves to retain fluid so that fluid flow is established along the length of the flow channel.

It is apparent that as the blood enters the flow channel and successively passes through each of the groove segments 26 through 34, air, previously occupying such space, must be vented. Accordingly, the present invention includes a vent means including at least one and in one embodiment two elongated vent channels 50, also formed in or on the exterior cylindrical surface 38 but being of a substantially reduced thickness or height along the base 12. The reduced cross-sectional area of vent channel 50 establishes a sufficient cross sectional dimension of the vent channels 50 to allow air to flow therethrough and exit to annular receiving chamber 51 located at one end of the vent channels 50. The opposite end of the vent groove 50 as at 50' is disposed in direct fluid receiving relation to an endmost groove segment 34. Groove segment 34 differs in configuration from the remainder of the groove segments 26 through 33 in that it completely surrounds the exterior cylindrical surface 38 in which it is formed, in an annular configuration.

The vent means further comprises a receiving chamber 51 disposed at the innermost end of the vent channels 50 as at 50" such that air and possibly blood will empty directly into the chamber 51. The receiving chamber 51 communicates with the vent ports 52 disposed in fluid communication with the interior cavity or hollow interior portion 60 extending into the interior of the base 12 and along a major portion of the length thereof and having an open end 62 (see FIGS. 5 and 6) which communicates with the exterior of the base 12 so as to pass any vented air leaving vent port 52 into cavity 60 to atmosphere.

As set forth above, the substantially lesser depth of vent grooves 50 into the surface 38 allows free air flow but restricts liquid flow. Accordingly, while the flow of blood through the flow channel will take a relatively short amount of time during a continuous blood flow condition, the passage of blood along the vent groove 50 will take a comparatively longer amount of time. This is to restrict or prevent blood passing through the vent port 52 and actually exiting into the central cavity 60 such as at 70. If a minimal amount of blood in fact reaches the interior cavity 60, such blood will quickly coagulate or alternately, take such a long time to fill the central cavity 60 that use of the base 12 and needle 14 will be ended since the catheter (not shown) will already be in place within the designated blood vessel.

The structural features of the subject flashback structure are such that entering blood passes in a circuitous path of fluid flow through the various groove segments along the length of the base 12 from the interior of the neede 14. As the blood passes along the path of fluid flow defined by the semiannular or semicircular groove segments, the air is forced from this path and in effect passes to the exterior of the base through the centrally disposed passage 60 and eventually out through open end 62. Conceivably, if the blood passing along the path of flow did not harden or coagulate, it too could pass into the interior of the central passage or chamber 60 and out through the open end 62. However, with the recent advent of diseases such as AIDS, there is a specific aversion to utilizing any instrument of the type set forth herein which actually allows or permits blood to leak therefrom. Accordingly, it has been found that the blood traveling specifically along the circuitous path defined by the semiannular segments serves to facilitate coagulation of the blood long prior to it reaching the receiving chamber 51 or vent port 52. Once the blood coagulates between the ends 50' and 50", the passage of blood will of course stop. While the dimensions of the air vent 50 are such as to effectively restrict liquid or blood flow therealong, the coagulation of the blood prior to entering the air vent 50 would of course eliminate any possibility of the blood passing into the central passage 60 and out through the open end 62 where it could possibly come into contact with medical personnel or patients.

Another safety feature associated with the present invention is the provision of supplementary receiving chambers 49 and 55 located at the distal end and proximal end respectively of the base 12. These supplementary receiving chambers are completely annular and are positioned so as to receive and hold any blood inadvertently leaking beneath the outer covering sleeve 44 from the next adjacent groove segment. More specifically, the distal-most supplementary receiving chamber 49 is disposed to retain and prevent leakage or passage of any blood inadvertently passing from the endmost groove segment 34 beneath the cover sleeve 44 from exiting from the end of the base 12. Instead, any such blood leaking from the groove segment 34 will be retained and effectively captured within the supplementary chamber 49.

Similarly, the position of the supplementary chamber 55 at the opposite end of the base 12 is disposed in a continuous annular configuration and further disposed to receive any blood inadvertently passing beneath the sleeve 44 from the chamber 20 as best shown in FIGS. 2, 3, 4 and 5.

Now that the invention has been described, what is claimed is:

1. A flashback structure of the type used to determine proper placement of a needle tip within a blood vessel, such as when placement of a catheter assembly within the blood vessel is being attempted, said structure comprising:
    (a) a base having an elongated configuration and an outer surface comprising a substantially elongated cylindrical configuration and including a needle extending outwardly from one end of said base, said needle terminating in a sharpened tip at a distal end thereof,
    (b) said needle comprising a hollow interior portion extending along the length thereof from said tip to a proximal end of said needle, said proximal end secured on the interior of said base, whereby blood travels along said needle into said base when said tip is located within said blood vessel,
    (c) a flow channel integrally formed on said outer cylindrical surface of said base and disposed in fluid communication with said needle at substantially one end of said base and a vent means at the opposite end of said flow channel relative to said needle,
    (d) said vent means formed at least in part on said cylindrical outer surface of said base for the exiting of air from said flow channel as blood enters therein from said needle,
    (e) said flow channel comprising a groove structure extending along at least a portion of the length of said base and comprising a plurality of groove segments,
    (f) said plurality of groove segments integrally formed in said cylindrical outer surface in spaced relation to one another and collectively extending between and in fluid communication with said proximal end of said needle and said vent means, (g) each of said groove segments comprising a curvilinear configuration disposed transversely to the length of said base in at least partially surrounding relation thereto and extending into said base a sufficient depth to allow a free flow of blood therealong, (h) cover means being at least partially transparent and mounted in engaging and surrounding relation to said cylindrical outer surface of said base and in covering, fluid retaining relation to said plurality of groove segments and said vent means, (i) at least one supplementary chamber formed in said cylindrical outer surface in spaced relation to an endmost groove segment at one end of said flow channel, said supplementry chamber being covered by said cover means and adapted to be in fluid communication with said flow channel between an inner surface of said cover means and said cylindrical outer surface in the event there is an imperfection on the cylindrical outer surface, and (j) whereby blood inadvertently leaking from said one end of said flow channel beneath said cover means will be retained within said supplementary receiving chamber.

2. An assembly as in claim 1 wherein said cover means comprises a sleeve dimensioned and configured for concentric, mating engagement about said cylindrical outer surface and further disposed in covering relation to said base at least along the length of said flow channel and said supplementary receiving chamber.

3. A flasback structure as in claim 2 wherein said groove structure and said plurality of groove segments are disposed to define a circuitous path of travel for said blood entering said flow channel and passing from said needle to said vent means.

4. A flashback structure as in claim 3 further comprising two supplementary receiving channels each located at a different opposite end of said flow channel and each adapted to be in fluid communication therewith only between an inner surface of said sleeve and said cylindrical outer surface in the event there is an imperfection on the cylindrical outer surface.

5. A flashback structure as in claim 4 wherein said vent means comprises at least one vent channel formed along said outer surface and connected at one end in fluid communicating relation with said flow channel and at the other end in fluid communicating relation with the exterior of said body, said vent channel having a cross-sectional area sufficient to allow flow of air and a restricted flow of blood therealong.

6. A flashback structure as in claim 5 wherein said vent channel is of a smaller cross-section than said groove segments and being sized to restrict the rate of liquid flow therealong from said flow channel towards an exterior of said base.

7. A flashback structure as in claim 5 wherein said vent means comprises two vent channels formed along said outer cylindrical surface in spaced, parallel relation to one another and each connected at one end in fluid communicating relation with said flow channel and at the other end thereof in fluid communication with the exterior of said body, each of said vent channels being defined in part by a separate vent channel integrally formed along said outer surface in spaced relation to said flow channel and being of a cross-sectional area sufficient to allow flow of air and a restrictive flow of blood therealong.

8. A flashback structure as in claim 7 wherein said cross-sectional area of each of said vent channels is of a limited, lesser cross-sectional area than that of said groove segments and sufficient to restrict the rate of liquid flow therealong from said flow channel towards an exterior of said base.

* * * * *